United States Patent [19]
Pawloski et al.

[11] Patent Number: 5,480,568
[45] Date of Patent: Jan. 2, 1996

[54] ALKYL ARYL SULFONES AND THEIR USE AS LUBRICANTS IN HIGH TEMPERATURE AND MAGNETIC RECORDING MEDIA APPLICATIONS

[75] Inventors: Chester E. Pawloski, Bay City; Bassam S. Nader, Midland, both of Mich.

[73] Assignee: The Dow Chemical Company, Midland, Mich.

[21] Appl. No.: 279,036

[22] Filed: Jul. 22, 1994

[51] Int. Cl.$^6$ .................................................. C10M 135/10
[52] U.S. Cl. ...................... 252/46.7; 252/47.5; 252/48.2; 252/48.4; 252/62.51 R; 427/128; 546/21; 546/26; 546/255; 546/261; 568/28; 568/33; 568/34; 568/35
[58] Field of Search ................................. 568/28, 34, 35; 252/48.2, 48.4, 46.7, 62.51; 427/128; 546/21, 26, 255, 261

[56] References Cited

U.S. PATENT DOCUMENTS

| | | | |
|---|---|---|---|
| 4,082,793 | 4/1978 | Nannelli et al. | 568/34 |
| 4,486,604 | 12/1984 | Konishi et al. | 568/33 |
| 4,545,812 | 10/1985 | Konishi et al. | 71/103 |
| 4,565,569 | 1/1986 | Konishi et al. | 71/103 |
| 4,705,718 | 11/1987 | Kitahata et al. | 252/62.51 |
| 4,870,213 | 9/1989 | Inbaasekaran et al. | 568/645 |
| 4,950,793 | 8/1990 | Souma | 568/28 |
| 5,009,925 | 4/1991 | Grigat et al. | 427/128 |
| 5,061,388 | 10/1991 | Nader | 200/47 |
| 5,066,409 | 11/1991 | Nader | 252/48.2 |
| 5,104,559 | 4/1992 | Pawloski et al. | 252/48.4 |
| 5,204,011 | 4/1993 | Nader | 252/48.4 |
| 5,235,084 | 8/1993 | Saito et al. | 568/34 |
| 5,275,879 | 1/1994 | Yoshida et al. | 252/62.51 |
| 5,340,489 | 8/1994 | Nader et al. | 252/48.4 |

OTHER PUBLICATIONS

"Friedel–Crafts Reactions of Methanesulfonyl Chloride with Benzene and Certain Substituted Benzenes", Truce et al., May 20, 1953, vol. 75, pp. 5032–5036.

Primary Examiner—Ellen M. McAvoy
Attorney, Agent, or Firm—John B. Treangen

[57] ABSTRACT

Alkyl aryl sulfones are disclosed which are useful as high temperature and magnetic recording media lubricants. Also disclosed are lubricating mixtures containing the alkyl aryl sulfones, magnetic recording media containing the alkyl aryl sulfones, and a process for lubricating the magnetic recording media with the alkyl aryl sulfones.

22 Claims, No Drawings

ALKYL ARYL SULFONES AND THEIR USE AS LUBRICANTS IN HIGH TEMPERATURE AND MAGNETIC RECORDING MEDIA APPLICATIONS

BACKGROUND OF THE INVENTION

The present invention is related to lubricants, more particularly, to lubricants useful for both magnetic recording media and high temperature applications.

The demands placed on existing lubricants are currently undergoing significant changes. New engines for automotive and aeronautic applications have requirements that differ dramatically from those previously known. Thus, what is needed are novel compounds that are useful as lubricant base stocks or as lubricant additives and are also stable at high use temperatures. Being stable at high use temperatures means that, as compared to non-stable compounds, the desired lubricating compounds: (1) have low reactivity at elevated temperatures, e.g., are less susceptible to oxidation, less hydrolyzable, less reactive to bases, and less polymerizable; (2) experience little or no decomposition at elevated temperatures; and (3) have relatively low volatility and high boiling points. It is desirable that lubricants be highly soluble in organic oils and greases if they are to be used as lubricant additives. It is also desirable that lubricants can be prepared by simple methods and in high yields.

In addition, lubricants are needed for use in magnetic recording media such as high density rigid disks, ultra high density floppy disks, digital audio tapes and video tapes which can be read by a magnetic recording head. In use of these media, a recording head is in very close proximity to the recording media and frequently contacts the recording media. Such contact causes wear of the thin layer of magnetic material on the recording media and shortens the useful life of the recording media. With insufficiently effective lubricants, there are problems including increased friction, scratching, and adhesion. Therefore, new efficient lubricants are desirable.

SUMMARY OF THE INVENTION

In one aspect, this invention is an alkyl aryl sulfone of the formula:

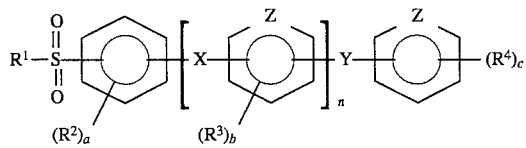

wherein Z is independently in each occurrence carbon or nitrogen;
$R^1$ is selected from the group $CH_3$ and $C_mF_{2m+1}$;
$R^2$ is independently in each occurrence a substituent selected from the group F, $C_mF_{2m+1}$, $OC_mF_{2m+1}$, phenyl, and phenoxy; a is 0 or an integer less than or equal to 4 inclusive;
$R^3$ is independently in each occurrence a substituent selected from the group F, $C_mF_{2m+1}$, $OC_mF_{2m+1}$, phenyl, and phenoxy; b is 0 or an integer less than or equal to 4 inclusive when Z is carbon, and 0 or an integer less than or equal to 3 inclusive when Z is nitrogen;

$R^4$ is independently in each occurrence a substituent selected from the group F, $C_mF_{2m+1}$, $OC_mF_{2m+1}$, and

c is 0 or an integer less than or equal to 5 inclusive;
n is 0 or an integer less than or equal to 5 inclusive;
m is an integer from 1 to 10 inclusive; and
X and Y are independently in each occurrence selected from the group: bond, O, $C(CH_3)_2$, $C(CF_3)_2$,

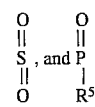

wherein $R^5$ is independently in each occurrence an alkyl having from 1 to 12 carbon atoms inclusive, or an aryl having from 1 to 12 carbon atoms inclusive.

In a second aspect, this invention is a lubricating mixture which comprises a lubricating fluid and an aforementioned alkyl aryl sulfone wherein the alkyl aryl sulfone is present in an amount sufficient to increase the lubricity of the lubricating fluid.

In a third aspect, this invention is a magnetic recording medium comprising a substrate having a magnetic recording lamina deposited thereon, wherein the lamina comprises magnetic particles and at least one aforementioned alkyl aryl sulfone, and wherein the alkyl aryl sulfone is present in an amount of at least 0.001 weight percent based on the total weight of the lamina.

In a fourth aspect, this invention is a process for lubricating a magnetic recording medium which comprises applying at least one aforementioned lubricating mixture to a surface of the magnetic recording medium to provide a lubricant film having an average thickness of 1 to 1000 angstroms ($10^{-10}$ to $10^{-7}$ meters) on the surface.

The alkyl aryl sulfones of this invention are useful in lubricating applications over a wide range of temperatures, such as between $-50°$ C. to $500°$ C. An application of current interest includes a use in magnetic recording media wherein the aforementioned alkyl aryl sulfone lubricant is incorporated as part of an internal or topical lubricant system. Incorporation of the alkyl aryl sulfone minimizes wear, improves overall performance, and protects the media from damage from the reading and/or writing head of a disk assembly such as high density rigid disks, ultra high density floppy disks, digital audio tape, 8 mm video tape, and super VHS tape.

DETAILED DESCRIPTION OF THE INVENTION

The alkyl aryl sulfones of this invention are those of the first aspect of this invention as described above.

These alkyl aryl sulfones always contain at least two aromatic six-membered rings when n is equal to zero, but can contain up to a total of thirteen aromatic rings if n is equal to 5 and both X and Y contain an $R^5$ that is aryl. Preferably, there are a total of no more than seven aromatic rings, more preferably, no more than five. When n is an integer from 1 to 5 inclusive, Z can independently in each occurrence be the same or different (i.e. carbon or nitrogen).

$R^1$ in the alkyl aryl sulfone of this invention is selected from the group methyl ($CH_3$) and perfluoroalkyl ($C_mF_{2m+1}$), wherein m is an integer from 1 to 10 inclusive. Preferably, m is no greater than 5, more preferably, no greater than 3. For purposes of this invention, it should be clear, and self-evident from the structures disclosed, that any reference to the substituents $R^1$ through $R^7$, X, and Y is to that of a radical or moiety of the substituent. In addition, any reference to the substituents $C_mF_{2m+1}$ or $OC_mF_{2m+1}$ is meant to include all straight chain and branched chain moieties. When $R^1$ is methyl ($CH_3$), preferably the alkyl aryl sulfone comprises a compound of the formula

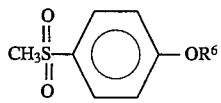

wherein $R^6$ is selected from the group Ph, $CF_3Ph$, FPh, 1,3-Ph, 1,4 Ph, PhOPh, FPhOPh, $CF_3PhOPh$, $CF_3OPhOPh$, Py, 2,4-Py, 6-($CF_3PhO$-2-Py), and 6-(FPhO-2-Py); and wherein Ph is phenyl, and Py is pyridyl. Examples of preferred compounds represented by this formula include: 1,3-bis( 4-(methylsulfonyl)phenoxy)benzene; 2,6-bis-di[4-(methylsulfonyl)phenoxy] pyridine; 2-(4-methylsulfonylphenoxy)- 6-(3-trifluoromethylphenoxy)pyridine; 2-phenoxy-6-(4-methylsulfonylphenoxy)pyridine; 4-(4-methylsulfonylphenoxy)benzophenone; 1-(4-methylsulfonyl)phenoxy)-4-phenoxy benzene; 1-( 4-methylsulfonylphenoxy)-3-(3-(trifluoromethyl)phenoxy-)benzene; and 1-(4-methylsulfonylphenoxy)-3-(3-(trifluoromethoxy)phenoxy)benzene.

When $R^1$ is perfluoroalkyl ($C_mF_{2m+1}$), the alkyl aryl sulfone preferably comprises a compound of the formula

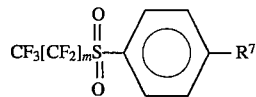

wherein $R^7$ is selected from the group consisting of PhO, PhOPhO, PhOPhOPhO, $CF_3PhO$, $CF_3PhOPhO$, $CF_3PhOPyO$, PhOPyO, FPhO, FPhOPhO, and $CF_3[CF_2]_mSO_2PhO$; m is an integer from 1 to 10 inclusive; and Ph and Py are as defined above. Examples of preferred compounds represented by this formula include: 1-(3-phenoxyphenoxy)-4-(trifluoromethylsulfonyl)benzene; 1-(3-trifluoromethylphenoxy)-3-(4-(trifluoromethylsulfonyl)phenoxy)benzene; bis(3-(4-trifluoromethylsulfonylphenoxy)phenyl) ether; 1,3-bis(4-(trifluoromethylsulfonyl)phenoxy)benzene; 2-phenoxy-6(4-(trifluoromethylsulfonyl)phenoxy)pyridine; benzene(4-(1,1,1,2,2-pentafluoroethylsulfonyl)phenoxy)-2-(3-trifluoromethylphenoxy) ; bis(4-(pentafluoroethylsulfonylphenoxyphenyl) ether; 1-(3-trifluoromethoxyphenoxy)-3-(4-trifluoromethylsulfonyl)phenoxy)benzene; and (3-(4-pentafluoroethyl-sulfonylphenoxy)phenyl)(3-phenoxyphenyl) ether.

$(R^2)_a$ and $(R^3)_b$ in the alkyl aryl sulfones of this invention are independently in each occurrence substituents selected from the group F, $C_mF_{2m+1}$, $OC_mF_{2m+1}$, phenyl, and phenoxy, wherein a is 0 or an integer less than or equal to 4 inclusive, and b is 0 or an integer less than or equal to 4 inclusive, when Z is carbon and an integer less than or equal to 3 inclusive, when Z is nitrogen. The phenyl and phenoxy may be substituted or unsubstituted. When substituted, the substituent group should be one that does not sterically hinder the compound. Examples of preferable substituents comprise F, $C_mF_{2m+1}$, and

wherein m and $R^1$ are the same as described above.

$(R^4)_c$ in the alkyl aryl sulfone of this invention is independently in each occurrence a substituent selected from the group F, $C_mF_{2m+1}$, $OC_mF_{2m+1}$, and

wherein c is 0 or an integer less than or equal to 5 inclusive, and m and $R^1$ are the same as described above.

X and Y in the alkyl aryl sulfone of this invention are independently in each occurrence selected from the group: bond, O, $C(CH_3)_2$, $C(CF_3)_2$,

wherein $R^5$ is independently in each occurrence an alkyl having from 1 to 12 carbon atoms inclusive, or an aryl having from 1 to 12 carbon atoms inclusive.

For example, some basic illustrations of the alkyl aryl sulfones of this invention wherein X and Y are oxygen (O), $R^2$ and $R^3$ are hydrogen (H), and n is 1, comprise:

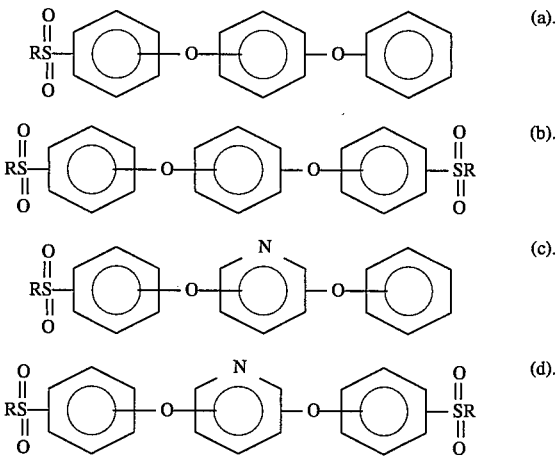

wherein R is $CH_3$ or $C_mF_{2m+1}$, and m is an integer from 1 to 10 inclusive. In (a) and (b), above, Z is carbon, and in (c) and (d), above, one Z is nitrogen.

Some specific illustrations of the alkyl aryl sulfones of this invention wherein z is carbon are as follows:

4-[4-(Methylsulfonyl)phenoxy]phenyl phenyl sulfone

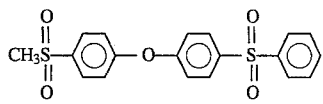

4-[4-(Trifluoromethylsulfonyl)phenoxy]phenyl phenyl sulfone

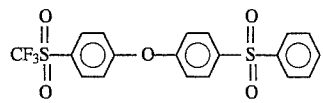

4,4'-Bis[4-(methylsulfonyl)phenoxy]phenyl sulfone

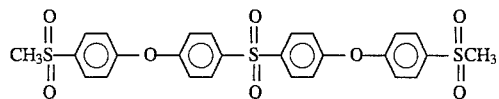

4,4'-Bis[4-(trifluoromethylsulfonyl)phenoxy]phenyl sulfone

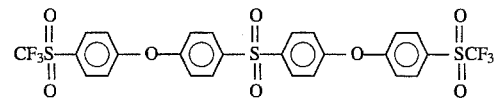

4,4'-Bis[4-(methylsulfonyl)phenoxy]phenyl phenyl phosphine oxide

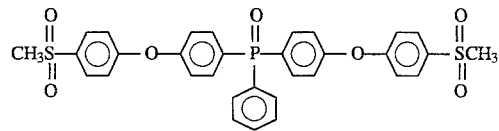

4,4'-Bis[4-(trifluoromethylsulfonyl)phenoxy]phenyl phenyl phosphine oxide

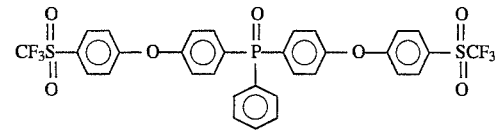

4,4'-Bis[4-(methylsulfonyl)phenoxy]phenyl methyl phosphine oxide

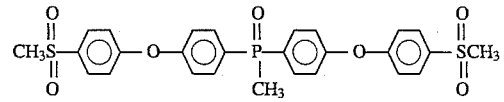

4,4'-Bis[4-(trifluoromethylsulfonyl)phenoxy]phenyl methyl phosphine oxide

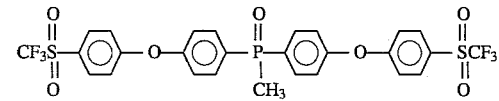

4-[4-(Methylsulfonyl)phenoxy]biphenyl

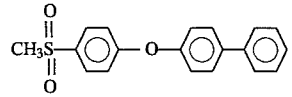

4-[4-(Trifluoromethylsulfonyl)phenoxy]biphenyl

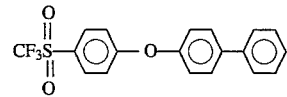

4,4'-Bis[4-(Methylsulfonyl)phenoxy]biphenyl

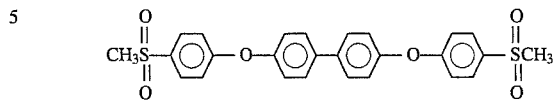

4,4'-Bis[4-(Trifluoromethylsulfonyl)phenoxy]biphenyl

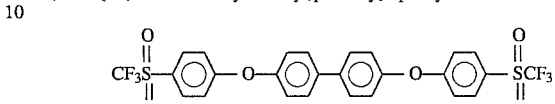

2-[4-(4-Methylsulfonylphenoxy)phenyl]-2-phenylpropane

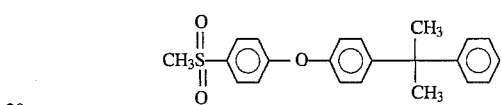

2-[4-(4-Methylsulfonylphenoxy)phenyl]-2-phenyl-1,1,1,3,3,3-hexafluoropropane

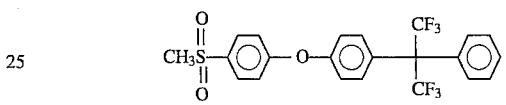

2,2-Bis[4-(4-methylsulfonylphenoxy)phenyl]propane

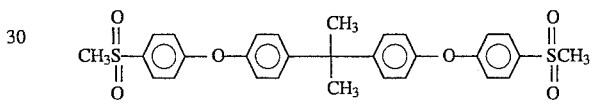

2,2-Bis[4-(4-methylsulfonylphenoxy)phenyl]-1,1,1,3,3,3-hexafluoropropane

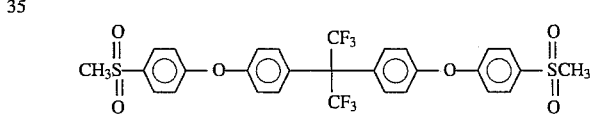

2-[4-(4-Trifluoromethylsulfonylphenoxy)phenyl]-2-phenylpropane

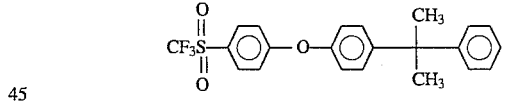

2-[4-(4-Trifluoromethylsulfonylphenoxy)phenyl]-2-phenyl-1,1,1,3,3,3-hexafluoropropane

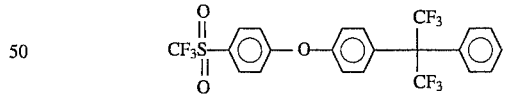

2,2-Bis[4-(4-trifluoromethylsulfonylphenoxy)phenyl]-propane

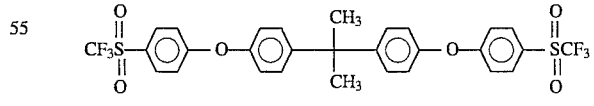

and 2,2-Bis[4-(4-trifluoromethylsulfonylphenoxy)phenyl]-1,1,1,3,3,3-hexafluoropropane

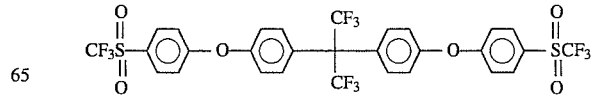

Generally, the alkyl aryl sulfones of this invention can be prepared by reacting an appropriate alkylsulfonylphenyl halide with an appropriate phenol in the presence of an appropriate base, under conditions such that the corresponding alkyl aryl sulfone is produced. Typically, the reaction is run under ambient pressures, although pressure is not critical and subatmospheric or superatmospheric pressures can be used. The reaction occurs at a temperature that will vary depending on starting materials and solvent. Typically, reaction temperature is in the range from 0° C. to 200° C. and is more typically the reflux temperature. The reaction preferably occurs in an inert atmosphere using an inert gas such as nitrogen. The reaction can be monitored by standard techniques, such as by gas chromatography, to determine completion of the reaction. The reaction is typically complete within 12 hours, although time may vary depending on such factors as amount and type of starting materials, presence of a catalyst, and temperature. The product alkyl aryl sulfones can be recovered and purified by standard techniques such as by filtration, recrystallization, distillation, and chromatography. Various specific examples of preparing these alkyl aryl sulfones are provided, below, in the "Examples" section.

The alkyl aryl sulfones of this invention are useful as lubricants over extended temperature ranges. They may be used alone as lubricating fluids and also may be used in conjunction with various additives. Additionally, they may themselves be used as additives with other lubricant fluids to form lubricant mixtures.

When used as an additive to a lubricant fluid, the alkyl aryl sulfones of the present invention must be compatible with the lubricant fluid. By compatible, it is meant that the compounds of the present invention may be readily dispersed or dissolved in the lubricant fluid, either with or without the addition of an appropriate surfactant. Examples of known lubricant fluids useful in conjunction with the alkyl aryl sulfones of this invention include hydrocarbon lubricants such as mineral oil; alpha-olefin fluids; silicone fluids and greases; polyalkyl ether fluids; perfluoroalkyl ethers and greases; ester lubricants such as pentaerythritol esters and trimethylol alkane esters; polyaryl ether fluids such as polyphenyl ether; and phosphazene fluids. Preferably, the lubricating fluid is a phosphazene compound or a polyaryl ether compound such as 5P4E which is a polyphenyl ether having five phenyl groups and four ether linkanges. Other preferred lubricant fluids include polyol esters such as pentaerythritol tetra $C_{5-9}$ esters, and poly alpha olefins.

When used as an additive in combination with another lubricating fluid, the alkyl aryl sulfones are employed in an amount sufficient to increase the lubricity (or antifriction effect) of the lubricating mixture. Preferably, the alkyl aryl sulfones are employed in a concentration, based on the weight of the lubricating fluid component, of at least about 0.1 percent, more preferably greater than about 0.5 percent, and most preferably greater than about 1 percent. Preferably, the alkyl aryl sulfones are employed in a concentration less than about 50 percent, more preferably less than about 20 percent, and most preferably less than about 10 percent. In order to form a lubricating mixture from the alkyl aryl sulfone and another lubricating fluid, the alkyl aryl sulfone is typically dissolved in an organic solvent such as methylene chloride and this solution is mixed with a solution of the lubricating fluid and an organic solvent to, thereby, admix the compounds. The mixture is preferably filtered to remove any solid impurities and the organic solvents are then removed from the lubricating mixture by methods such as evaporation or distillation. The alkyl aryl sulfones can also be added directly to the lubricating fluid followed by admixing to disperse the alkyl aryl sulfones.

In addition, the alkyl aryl sulfones of this invention can be used alone as a lubricating fluid. When used in this capacity in high temperature applications such as in lubricating aircraft turbines, the alkyl aryl sulfones of this invention are advantageously thermally and oxidatively stable.

A preferred application of the alkyl aryl sulfones of this invention is their use in magnetic recording media. Magnetic recording media using the alkyl aryl sulfones of this invention typically comprise a substrate having a particulate or thin film magnetic recording lamina deposited thereon, the lamina comprising magnetic particles with a binder in the case of particulate media or without a binder in the case of thin film media. The lamina includes a lubricating amount of one or more alkyl aryl sulfones used as either an internal or topical lubricant. Preferably, the alkyl aryl sulfone is present in an amount of at least 0,001 weight percent, but less than about 20 weight percent, based on the total weight of the lamina.

The alkyl aryl sulfones of this invention are particularly useful as topical lubricants for thin film, or non-porous hard and flexible magnetic recording media. Thin film magnetic recording media generally include a substrate which may be a non-magnetic metal or a plastic such as a polyester (e.g. polyethylene terephthalate). A magnetic film such as a metal or a metal alloy such as cobalt-nickel is then applied to the substrate. The thickness of the magnetic layer is on the order of 0.20 micrometer. The one or more alkyl aryl sulfone are preferably deposited on the surface of the magnetic layer in a thickness of from about 1 to about 2000 Angstroms ($10^{-10}$ to $10^{-7}$ meters (m)), more preferably from about 20 to about 1000 Angstroms.

Similarly, the alkyl aryl sulfones are useful in particulate magnetic recording media. Particulate magnetic recording media generally include a substrate which may be a non-magnetic metal or a plastic such as a polyester. Magnetic particle containing pigments such as cobalt gamma iron oxide, barium ferrite, and iron metal with a binder, are applied to the substrate. The amount of pigment can vary from about 17 to about 21 weight percent based on total magnetic recording medium formulation weight and a preferred range of from about 17 to about 19 weight percent. The binder is advantageously a thermosetting resin such as resins of urethane, vinyl, or a combination thereof, present in an amount between about 2.5 and about 7.0 weight percent, based on total formulation weight and a preferred range between about 3.0 and about 6.0 weight percent.

When used as a topical lubricant for either particulate or thin film media, the alkyl aryl sulfone is conveniently applied to the surface either directly or in solution with a volatile solvent. Representative examples of volatile solvents for alkyl aryl sulfones include: aromatic hydrocarbons such as benzene, toluene, and xylene; ethers such as diethyl ether, dimethoxyethane, dioxane, tetrahydrofuran and diethoxyethane; halogenated hydrocarbons such as chloroform, dichloromethane and carbon tetrachloride; alcohols such as methanol and ethanol; ketones such as methyl ethyl ketone and acetone; esters such as ethyl acetate; alicyclic hydrocarbons such as cyclohexane; dimethylformamide; dimethylsulfoxide; and silicone fluids.

Alternatively, when used as an internal lubricant in particulate magnetic media, the alkyl aryl sulfone is included as a component of a mixture that is applied to the substrate to form the recording lamina. This mixture includes a binder, a pigment containing magnetic particles, and a volatile solvent together with the alkyl aryl sulfone. Representative solvents for the alkyl aryl sulfone include those listed for topical uses.

The following examples are provided to illustrate the invention and should not be interpreted as limiting the scope of the invention. Unless stated otherwise, all parts and percentages are given by weight and all percent yields (% yield) are based on theoretical. All apparatus are rigorously dried and flushed with nitrogen before use. Melting points are determined in open capillary tubes, and are uncorrected.

In the Examples, Pressure Differential Scanning Calorimetry (PDSC) was used to determine the thermooxidative stability of the products. The PDSC runs were performed on a DuPont Instruments 910 Differential Scanning Calorimeter with a DuPont Instruments 1090B Thermal Analyzer control unit using aluminum pans. A constant oxygen pressure of $1.38 \times 10^6$ Pascal (200 psi) and flow rate of 50 cubic centimeters ($cm^3$) per minute were also used. The instrument was programmed to raise the temperature at a rate of 15° C. per minute. The PDSC temperature reported is that temperature at which oxidation of the product begins.

EXAMPLE 1

This example illustrates the preparation of several types of perfluoroalkylsulfonylphenyl ethers. Each of these illustrated ethers are produced in (a)–(e), below. Unless otherwise indicated, the reactions described below are performed in a 250 mL, 3-necked flask equipped with a mechanical stirrer, a reflux condenser topped with a nitrogen inlet tube, and a stopper. These illustrations utilize a starting material of 1-chloro-4-(trifluoromethylsulfonyl)benzene which may be prepared as described below. First, 1-chloro-4-trifluoromethylthiobenzene is prepared as follows:

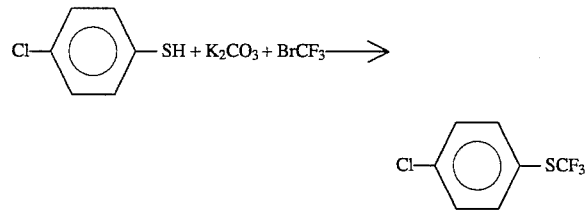

A mixture was formed in the flask from the following materials: 73 grams (g) of 4-chlorothiophenol, 400 milliliters (mL) of dimethyl formamide (DMF), and 70 g of potassium carbonate ($K_2CO_3$). This mixture was stirred at 60° C. for one hour and cooled to ice water bath temperatures (between about 0° C. and about 5° C.) and 100 g of bromotrifluoromethane ($BrCF_3$) was bubbled into the mixture for two hours. The mixture was then stirred for two hours while warming to room temperature (about 23° C.) and then poured into 300 mL of water with stirring to form a product. The product was extracted with 300 mL of methylene chloride, separated, and washed with 250 mL of water. The product-containing, methylene chloride phase was separated and then dried by passing it through sodium sulfate. Low boiling point (up to 100° C., unless stated otherwise) components of the product phase ("low boilers") were then distilled off under reduced pressure (about 0.5 mm Hg) and the remaining product was then distilled over a short distillation column under reduced pressure to produce an 80% yield of an oily product. The identity of the product was confirmed by gas chromatography-mass spectroscopy (GC-MS) spectra to be 1-chloro-4-trifluoromethylthiobenzene.

Then, 1-chloro-4-(trifluoromethylsulfonyl)benzene was prepared as follows:

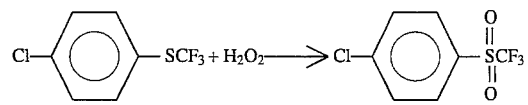

74 g of the 1-chloro-4-trifluoromethylthiobenzene was placed into a flask with 500 mL of glacial acetic acid and stirred to form a mixture. While stirring, 300 mL of a 30% hydrogen peroxided ($H_2O_2$)/water solution was added dropwise. After this addition, the mixture was stirred at reflux for several hours then cooled to room temperature. After cooling, the solids were filtered off and dried to produce 37 g of a product ("first product solids") having a melting point of 56°–57° C. GC-MS spectra confirmed a product of -chloro-4-(trifluoromethyl-sulfonyl)-benzene. The liltrate from filtering the solids was stirred with 300 mL of water and the product was extracted with 250 mL of methylene chloride to form an aqueous phase and a product-containing methylene chloride phase. The product-containing phase was separated, dried by passing it through sodium sulfate, low boilers were distilled off, and the remaining product was distilled to produce 15 g of product. This 15 g of product was then combined with the first product solids for a total yield of 57%.

(a) Preparation of 1-(3-PHENOXYPHENOXY)-4-(TRIFLUOROMETHYLSULFONYL)BENZENE

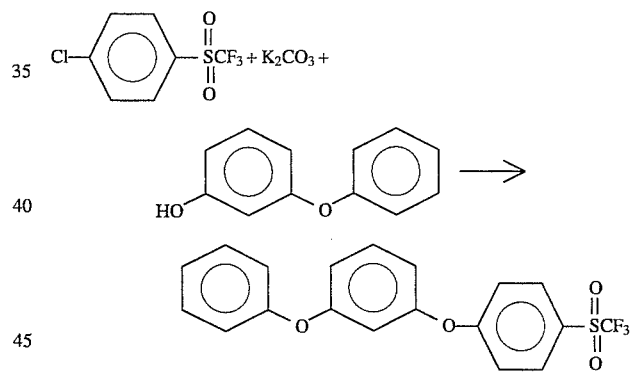

6.1 g Of the 1-chloro-4-(trifluoromethylsulfonyl)benzene was placed into a flask with 5 g of potassium carbonate, 10 g of 3-phenoxyphenol (Eastman Kodak, now Eastman Chemical Company), 100 mL of dimethyl sulfoxide (DMSO), and stirred to form a mixture. While stirring, this mixture was heated to 120° C. and an exotherm occurred. The product was stirred at 120° C. for a total of two hours. Gas chromatography (GC) analysis showed complete reaction. After cooling to room temperature, the reaction mixture was poured into 400 mL of water and the product was extracted with 200 mL of methylene chloride to form a product phase. The product phase was separated, dried by passing through sodium sulfate, low boilers were distilled off, and the remaining product distilled. The product distilled at 180°–190° C. at 0.5 mm Hg to produce an oil in 64% yield. The identity of the product was confirmed by GC-MS analysis as 1-(3-phenoxyphenoxy)-4-(trifluoromethylsulfonyl)benzene. PDSC of the product indicated an oxidative stability up to 349° C. under 200 psi oxygen pressure, suggesting a high degree of thermo-oxidative stability.

(b) Preparation of 1-(3-TRIFLUOROMETHYLPHENOXY)-3-(4-(TRIFLUOROMETHYLSULFONYL)PHENOXY)BENZENE

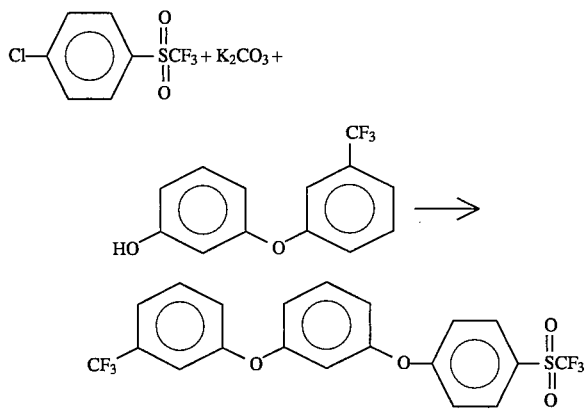

100 mL of methanol and 10 g of sodium were placed into a pre-dried (under nitrogen), 500 mL 3-necked flask equipped with a mechanical stirrer, a reflux condenser topped with a nitrogen inlet tube, and a stopper. After all of the sodium had been consumed, the methanol was distilled from the flask, and the last traces were removed by azeotropic distillation with benzene. Anhydrous pyridine (250 mL) and resorcinol (35 g) were added, followed by 3-bromobenzotrifluoride (50 g) and cuprous chloride (20 g), and the mixture was left to stir at reflux for 24 hours. The mixture was cooled and filtered with the aid of ether (200 mL). The ether-containing phase was washed successively with water (250 mL), 5% hydrochloric acid (2×500 mL), saturated sodium bicarbonate (200 mL), and saturated sodium chloride (200 mL). Then it was dried with magnesium sulfate, filtered, and solvent was removed on a rotary evaporator to leave 38 g of a dark oily residue. Fractional distillation in vacuo afforded 25.2 g (45% yield) of 3-(3-trifluoromethylphenoxy)phenol as a faintly yellowish oil distilling at 132° C. and 1.5 mm Hg. The identity of the product was confirmed by infrared (IR) and nuclear magnetic resonance (NMR) spectroscopies.

6.1 g of the 1-chloro-4-(trifluoromethylsulfonyl)benzene was placed into a flask with 5 g of potassium carbonate, 100 mL of DMSO, 12 g of the 3-(3-trifluoromethylphenoxy)phenol, and stirred to form a mixture. This mixture was processed as in (a) to produce a 67% yield of an oil. The identity of the product was confirmed by GC-MS as 1-(3-trifluoromethylphenoxy)- 3-(4-(trifluoromethylsulfonyl)phenoxy)benzene. PDSC of the product indicated an oxidative stability up to 375° C. under 200 psi oxygen pressure, suggesting a high degree of thermo-oxidative stability.

(c) Preparation of BIS(3-(4-TRIFLUOROMETHYL-SULFONYLPHENOXY)PHENYL) ETHER

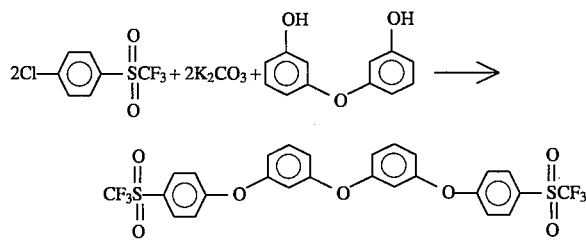

8.7 g of 1-chloro-4-trifluoromethylsulfonylbenzene was placed into a flask with 3 g of bis(3-hydroxyphenyl)ether (Aldrich Chemical Company), 100 mL of DMSO, 5 g of potassium carbonate, and stirred to form a mixture. This mixture was processed as in (a) to produce 4.6 g of an oil. PDSC of the product indicated an oxidative stability up to 356° C. under 200 psi oxygen pressure, suggesting a high degree of thermo-oxidative stability. The identity of the product was confirmed by GC-MS as bis(3-(4-trifluoromethylsulfonylphenoxy)phenyl) ether.

(d) Preparation of 1,3-BIS(4-TRIFLUOROMETHYL-SULFONYL)PHENOXY)BENZENE

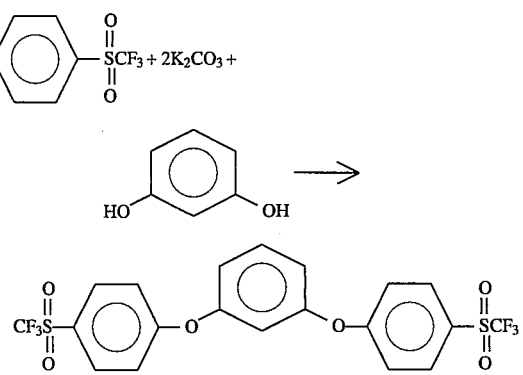

10 g of 1-chloro-4-trifluoromethylsulfonylbenzene was placed into a flask with 7 g of potassium carbonate, 50 mL of DMSO, 2.2 g of 1,3-dihydroxybenzene (Aldrich Chemical Company), and stirred to form a mixture. This mixture was processed as in (a) to produce 8.8 g of a wax. PDSC of the product indicated an oxidative stability up to 370° C. under 200 psi oxygen pressure, suggesting a high degree of thermo-oxidative stability. The identity of the product was confirmed by GC-MS as 1,3-bis(4-(trifluoromethylsulfonyl)phenoxy)benzene.

(e) Preparation of 2-PHENOXY-6-(4-(TRIFLUORO-METHYLSULFONYL)PHENOXY)PYRIDINE

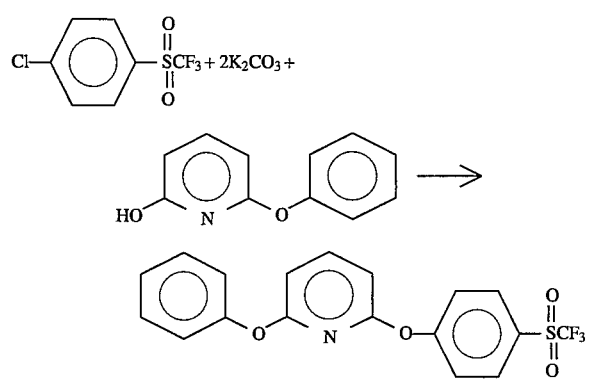

5 g of 1-chloro-4-trifluoromethylsulfonylbenzene was placed into a flask with 3.7 g of 6-phenoxy- 2-pyridinol (Aldrich Chemical Company), 50 mL of DMSO, 3 g of potassium carbonate, and stirred to form a mixture. This mixture was processed as in (a) to produce 3.6 g of an oil. PDSC of the product indicated an oxidative stability up to 330° C. under 200 psi oxygen pressure, suggesting a high degree of thermo-oxidative stability. The identity of the product was confirmed by GC-MS as 2-phenoxy- 6-(4-(trifluoromethylsulfonyl)phenoxy)pyridine.

EXAMPLE 2

This example illustrates the preparation of pentafluoroethylsulfones using iodopentafluoroethane as a starting material. Each of these pentafluoroethylsulfones are produced in (a)–(c), below. The reactions described below are all performed in the 250 mL, 3-necked flask as described in Example 1. These illustrations also utilize a starting material of 1-chloro-4-(1,1,1,2,2-pentafluoroethylsulfonyl)benzene which may be prepared as described below. First, 1-chloro-4-(1,1,1,2,2-pentafluoroethylthio)benzene was prepared as follows:

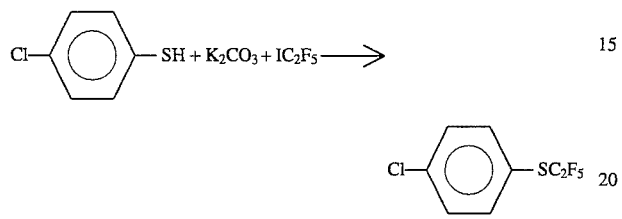

A mixture was formed in a flask from the following materials: 44 g of 4-chlorothiophenol, 48 g of potassium carbonate, and 200 mL of DMF. This mixture was stirred at 70° C. for one hour and cooled to ice bath temperatures while 100 g of iodopentafluoroethane were bubbled into the mixture. After this addition, the mixture was stirred for two hours and allowed to warm to room temperature. The mixture was poured into 500 mL of water and a product phase was extracted with 300 mL of methylene chloride. The product phase was dried by passing it through sodium sulfate and low boilers were distilled off. The remaining product was then distilled at 80°–85° C. and 20 mm Hg to produce an 81% yield. The identity of the product was confirmed by GC-MS spectra to be 1-chloro-4-(1,1,1,2,2-pentafluoroethylthio)benzene.

Then, 1-chloro-4-(1,1,1,2,2-pentafluoroethylsulfonyl)benzene was prepared as follows:

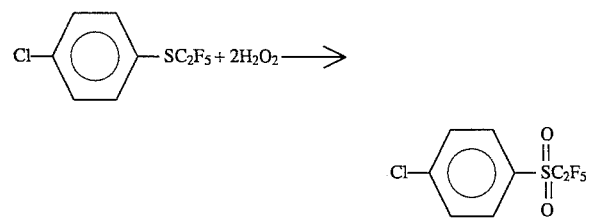

64 g of 1-chloro-4-(1,1,1,2,2-pentafluoroethylthio)benzene and 250 mL of glacial acetic acid were placed into a flask and stirred to form a mixture. While stirring, 250 mL of a 30% $H_2O_2$/water solution was added dropwise. After this addition, the mixture was stirred for four hours at reflux and allowed to cool to room temperature. GC analysis showed reaction was complete. The resulting solids ("first product solids") were filtered off and rinsed with water. The filtrate was poured into 500 ml of water, stirred, and extracted with 300 mL of methylene chloride to form an aqueous phase and a methylene chloride product phase. The methylene chloride product phase was separated, dried by passing it through sodium sulfate, and low boilers were distilled off. The resulting product phase was combined with the first product solids and distilled at 80°–85° C. and 1.0 mm Hg to produce a total of 62 g of white solids having a melting point of 37°–38° C. The white solids were confirmed by GC-MS analysis as 1-chloro-4-(1,1,1,2,2-pentafluoroethylsulfonyl)benzene.

(a) Preparation of BENZENE-(4-(1,1,1,2,2-PENTAFLUORO-ETHYLSULFONYL)PHENOXY)-2-(3-TRIFLUOROMETHYLPHENOXY)

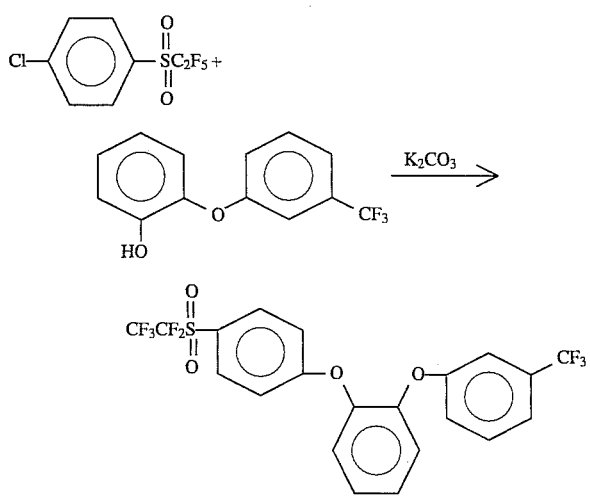

2-(3-trifluoromethylphenoxy)phenol was prepared by a procedure identical to the one described above for preparing 3-(3-trifluoromethylphenoxy)phenol, with the exception that catechol (Aldrich Chemical Company) is used in place of resorcinol.

8 g of the 1-chloro-4-pentafluoroethylsulfonylbenzene, was placed into a flask with 6.4 g of the 2-(3-trifluoromethylphenoxy)phenol, 5 g of potassium carbonate, and 50 mL of DMSO. This mixture was stirred at 120° C. for six hours. GC analysis showed complete reaction. After cooling to room temperature, the reaction mixture was poured into 400 mL of water and a product phase was extracted with 200 mL of methylene chloride. The product phase was separated, dried by passing through sodium sulfate, low boilers were distilled off, and the remaining product was distilled. The product distilled at 185°–195° C. and 0.5 mm Hg to produce 9 g of an oil. This oil product had a PDSC oxidative stability up to 330° C. under 200 psi oxygen pressure, suggesting a high degree of thermo-oxidative stability. The identity of the product was confirmed by GC-MS analysis as benzene-(4-(1,1,1,2,2-pentafluoroethylsulfonyl)phenoxy)- 2-(3-trifluoromethylphenoxy).

(b) Preparation of BIS(4-(PENTAFLUOROETHYL-SULFONYLPHENOXYPHENYL) ETHER

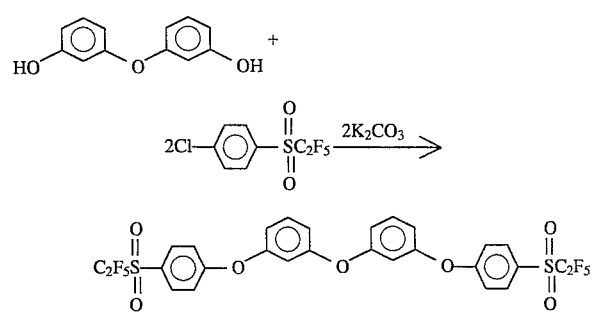

10 g of the 1-chloro-4-(pentafluoroethylsulfonyl)benzene was placed into a flask with 3 g of bis(3-hydroxyphenyl) ether (Aldrich Chemical Company), 100 mL of DMSO, 5 g of potassium carbonate, and stirred at 120° C. for six hours to form a mixture. This mixture was processed as in (a) to produce 7.4 g of wax. PDSC of the product indicated an oxidative stability up to 340° C. under 200 psi oxygen pressure, suggesting a high degree of thermo-oxidative stability. The identity of the product was confirmed by GC-MS analysis as bis(4-(pentafluoroethylsulfonylphenoxyphenyl) ether.

(c) Preparation of (3-(4-PENTAFLUOROETHYL-SULFONYLPHENOXY)PHENYL)(3-PHENOXYPHENYL) ETHER

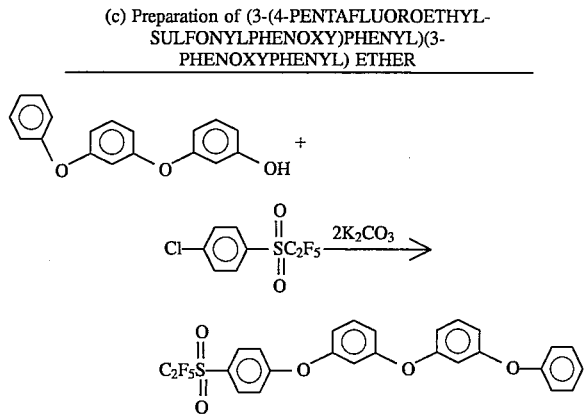

6 g of the 1-chloro-4-(pentafluoroethylsulfonyl)benzene was placed into a flask with 5.6 g of 3-(3-phenoxyphenoxy)phenol (Aldrich Chemical Company), 4 g of potassium carbonate, 50 mL of DMSO, and stirred at 120° C. for six hours to form a mixture. This mixture was processed as in (a) to produce 5.7 g of an oil. PDSC of the product indicated an oxidative stability up to 315° C. under 200 psi oxygen pressure, suggesting a high degree of thermo-oxidative. The identity of the product was confirmed by GC-MS analysis as (3-(4-pentafluoroethylsulfonylphenoxy)phenyl)(3-phenoxyphenyl) ether.

EXAMPLE 3

This example illustrates the preparation of several types of methylsulfonylaryl ethers. Each of these illustrated ethers are produced in (a)–(n), below. The reactions described below are all performed in the 250 mL, 3-necked flask as described in Examples 1 and 2.

(a) Preparation of 1-CHLORO-4-METHYLSULFONYL-BENZENE

Using a "Friedel-Crafts Reaction" procedure similar to that outlined in the Journal of the American Chemical Society, volume 75, page 5032 (1953), incorporated herein by reference, 100 mL of chlorobenzene and 47 g of aluminum chloride were placed in a flask and mixed. The mixture was then stirred while 46 g of methanesulfonyl chloride were added dropwise. The mixture was then stirred at 90° C. for four hours. GC analysis showed reaction took place. The reaction mixture was poured into 500 mL of ice water with stirring and a product was extracted with 300 mL of methylene chloride to form a product phase. The product phase was separated, washed with 250 mL of water, separated, dried by passing it through sodium sulfate, and low boilers were distilled off. The remaining product was distilled at 145°–55° C. and 0.5 mm Hg to produce 31.4 g of solids. GC analysis showed this to be a mixture of isomers. The product was heated with 100 mL of ethanol until a solution was obtained. On standing, 16.4 g of solids, having a melting point of 90°–93° C., were obtained. GC-MS showed this to be a 98% para isomer of 1-chloro-4-methylsulfonylbenzene. Solvent removal produced 12.8 g of solids in a 57% para isomer to 43% ortho isomer mixture.

(b) Preparation of 1-CHLORO-4-METHYLTHIOBENZENE

Into a flask were placed 100 g of 4-chlorothiophenol (Aldrich Chemical Company), 300 mL of DMSO, 110 g of potassium carbonate, and 115 g of methyl iodide. The contents of the flask were stirred at 45° C. for fourteen hours to form a reaction mixture. GC analysis showed reaction took place. After cooling to room temperature, the reaction mixture was poured into 500 mL of ice water with stirring. The resulting product was taken up in 500 mL of methylene chloride to form a product phase which was then separated and washed with 500 mL of water. The product phase was separated from the water, dried by passing it through sodium sulfate, and distilled to produce 83 g of an oil in a 75% yield. The identity of the product was confirmed by GC-MS to be 1-chloro-4-methylthiobenzene.

(c) Preparation of 1-CHLORO-4-METHYLSULFONYL-BENZENE

Into a flask were placed 10 g of 1-chloro-4-methylthiobenzene (formed in (b)), 50 mL of glacial acetic acid, and 30 mL of a 30% H$_2$O$_2$/water solution to form a mixture. This mixture was stirred at 90° C. for two hours. Low boilers were distilled off under reduced pressure and 200 mL of water was added to the remaining mixture with stirring. Solids were obtained. The solids were filtered off and taken up in 200 mL of methylene chloride to form a product phase. This product phase was washed with 150 mL of water, separated, and dried by passing through sodium sulfate. The product distilled at 125° C. and 0.5 mm Hg to produce 11 g of solids. GC-MS analysis showed this product to be at least 99% 1-chloro-4-methylsulfonylbenzene.

(d) Preparation of 4-METHYLSULFONYLPHENOL

Into a flask were placed 46 g of 4-methylthiophenol (Aldrich Chemical Company) and 250 mL of glacial acetic acid to form a mixture. This mixture was stirred while 150 mL of a 30% H$_2$O$_2$/water solution was added dropwise. After this addition, the mixture was stirred at 90°–100° C. for four hours. Low boilers were distilled off up to 125° C. and 0.5 mm Hg and a resulting oil was poured into 200 mL of toluene with stirring. 300 mL of n-hexane was added to this and solids were formed. The resulting solids were then filtered off and dried in sodium sulfate to produce 56 g of a solid having a melting point of 87°–90° C. GC-MS analysis showed a product of 4-methylsulfonylphenol in an 84% yield.

(e) Preparation of 1,3-BIS(4-(METHYLSULFONYL)PHENOXY)BENZENE

Into a flask were placed 2.8 g of 1,3-dihydroxybenzene, 10 g of potassium carbonate, 10.5 g of the 1-chloro-4-methylsulfonylbenzene (formed in (c)) and 100 mL of DMSO and a mixture was formed. This mixture was stirred at 140° C. for 14 hours. After cooling to room temperature, the flask was filled with water and the product extracted with 200 mL of methylene chloride to form a product phase. The product phase was separated and washed with 250 mL of water, separated, dried by passing through sodium sulfate, and heated to 150° C. and 1.0 mm Hg to form a solid product. The resulting solids were recrystallized from toluene/ethanol to give 6.6 g of solid having a melting point of 127°–129° C. GC-MS analysis showed a product of 1,3-bis(4-(methylsulfonyl)phenoxy)benzene.

(f) Preparation of 2,6-BIS-DI[4-(METHYLSULFONYL)PHENOXY] PYRIDINE

Into a flask were placed 2.9 g of 2,6-difluoropyridine (Aldrich Chemical Company), 50 mL of DMSO, 8.6 g of the 4-methylsulfonylphenol (formed in (d)), and 7 g of potassium carbonate to form a mixture. This mixture was stirred at 100° C. for 14 hours. GC analysis showed a reaction took place. The flask was filled with water and the product extracted with 300 mL of methylene chloride to form a product phase. The product phase was separated, passed through sodium sulfate, and low boilers were distilled off up to 160° C. and 0.5 mmHg. The resulting solids were stirred with 100 mL of toluene at reflux. The insolubles were filtered off and dried to produce 8.9 g of a tan solid having a melting point of 172°–173° C. PDSC of the product indicated an oxidative stability up to 368° C. under 200 psi oxygen pressure, suggesting a high degree of thermo-oxidative stability. GC-MS analysis confirmed the identity of the product to be 2,6-bis-di[4-(methylsulfonyl)phenoxy] pyridine having a purity of at least 98%.

(g) Preparation of 2-FLUORO-6-(4-METHYLSULFONYLPHENOXY)PYRIDINE

Into a flask were placed 51 g of 4-methylsulfonylphenol (formed in (d)), 34 g of 2,6-difluoropyridine (Aldrich Chemical Company), 42 g of potassium carbonate, and 300 mL of DMSO to form a mixture. This mixture was stirred at 120° C. for four hours. GC analysis showed that reaction took place. The flask was filled with water while stirring and the product extracted with 300 mL of methylene chloride to form a product phase. This product phase was washed with 300 mL of water, separated, passed through sodium sulfate and distilled. A solid product of 54 g resulted and was confirmed by GC-MS to be 2-fluoro-6-(4-methylsulfonylphenoxy)pyridine in a 67% yield.

(h) Preparation of 2-(4-METHYLSULFONYLPHENOXY)-6-(3-TRIFLUOROMETHYLPHENOXY)PYRIDINE Into a flask were placed 67 g of 2-fluoro-6-(4-methylsulfonylphenoxy)pyridine (formed in (g)), 50 g of 3-trifluoromethylphenol (Aldrich Chemical Company), 40 g of potassium carbonate, and 200 mL of DMSO to form a mixture. This mixture was stirred at 130° C. for four hours. GC analysis showed reaction took place. After cooling to room temperature, the flask was filled with water and stirred. The product was taken up in 400 mL of methylene chloride to form a product phase. The product phase was passed through sodium sulfate and distilled to produce 94 g of an oil. GC-MS analysis showed a 92% yield of 2-(4-methylsulfonylphenoxy)-6-(3-trifluoromethylphenoxy)pyridine.

(i) Preparation of 2-PHENOXY-6-(4METHYLSULFONYLPHENOXY)PYRIDINE

Into a flask were placed 4.8 g of 6-phenoxy-2-fluoropyridine (Aldrich Chemical Company), 4.4 g of 4-methylsulfonylphenol (formed in (d)), 4 g of potassium carbonate, and 50 mL of DMSO to form a mixture. This mixture was stirred at 130° C. for 10 hours. GC analysis showed reaction took place. The flask was filled with water while stirring. The product was taken up in 150 mL of methylene chloride to form a product phase. The product phase was passed through sodium sulfate and distilled on a Kugelrohr apparatus to produce 5.8 g of a solid distilling over at 220° C. and 0.5 mm Hg. GC-MS analysis showed a 68% yield of 2-phenoxy-6-(4-methylsulfonylphenoxy)pyridine.

(j) Preparation of 2-FLUORO-6-(4-FLUOROPHENOXY)PYRIDINE

Into a flask were placed 58 g of 2,6-difluoropyridine (Aldrich Chemical Company), 62 g of 4-fluorophenol (Aldrich Chemical Company), 76 g of potassium carbonate, and 300 mL of DMSO to form a mixture. This mixture was stirred at 130° C. for four hours. GC analysis showed that reaction took place. The flask was filled with water and the product extracted with 500 mL of methylene chloride to form a product phase. The product phase was washed with 300 mL of water, separated, and passed through sodium sulfate. The product distilled at 105°–125° C. and 0.5 mm Hg to produce 93 g of solids. GC-MS analysis showed an 87% yield of 2-fluoro-6-(4-fluorophenoxy)pyridine.

(k) Preparation 2-FLUORO-6-(3-TRIFLUOROMETHYLPHENOXY)PYRIDINE

Into a flask were placed 60 g of 2,6-difluoropyridine (Aldrich Chemical Company), 81 g of 3-trifluoromethylphenol (Aldrich Chemical Company), 70 g of potassium carbonate, and 150 mL of DMSO to form a mixture. This mixture was stirred at 130° C. for four hours and then processed as in (j) to produce 94 g of oil. GC-MS analysis showed a 73% yield of 2-fluoro-6-( 3-trifluoromethylphenoxy)pyridine.

(l) Preparation 4-(4-METHYLSULFONYLPHENOXY)BENZOPHENONE

Into a flask were placed 6 g of 4-hydroxybenzophenone (Aldrich Chemical Company), 100 mL of DMSO, 6 g of 4-fluoro-1-methylsulfonylbenzene (Aldrich Chemical Company), and 5 g of potassium carbonate to form a mixture. This mixture was stirred at 130°–140° C. for four hours and then processed as in (j) to produce 9.3 g of solids having a melting point of 159°–161° C. PDSC of the product indicated an oxidative stability up to 356° C. under 200 psi oxygen pressure, suggesting a high degree of thermo-oxidative stability. GC-MS analysis showed an 88% yield of 4-(4-methylsulfonyl-phenoxy)benzophenone.

(m) Preparation of 1-(4-METHYLSULFONYL)PHENOXY)-4-PHENOXYBENZENE

Into a flask were placed 1.9 g of 4-phenoxyphenol (Aldrich Chemical Company), 50 mL of DMSO, 2 g of potassium carbonate, and 2 g of 1-chloro-4-methylsulfonylbenzene (formed in (c)), to form a mixture. This mixture was stirred at 140° C. for 14 hours and then processed as in (j) to produce 1 g of solid having a melting point of 139°–141° C. PDSC of the product indicated an oxidative stability up to 351° C. under 200 psi oxygen pressure, suggesting a high degree of thermo-oxidative stability. GC-MS analysis showed the solid to be 1-(4-methylsulfonyl)phenoxy)-4-phenoxybenzene.

(n) Preparation of 1-(4-METHYLSULFONYL-PHENOXY)-3-(3-(TRIFLUOROMETHYL)PHENOXY)BENZENE Into a flask were placed 5 g of 3-(trifluoromethylphenoxy)phenol (Aldrich Chemical Company), 4 g of 1-chloro-4-methylsulfonylbenzene (formed in (c)), 4 g of potassium carbonate, and 75 mL of DMSO to form a mixture. This mixture was stirred at 140° C. for four hours and then processed as in (j) to produce 4.5 g of an oil. PDSC of the product indicated an oxidative stability up to 335° C. under 200 psi oxygen pressure, suggesting a high degree of thermo-oxidative stability. GC-MS analysis showed the oil to be 1-(4-methylsulfonylphenoxy)- 3-(3-(trifluoromethyl)phenoxy)benzene.

EXAMPLE 4

This example illustrates a Four-Ball lubricity test conducted on four different compositions. The Four-Ball lubricity tests measured lubricity characteristics on a Falex Model #6 Friction and Wear Tester equipped with a controlled temperature holding cup. The tests were performed at 300° C., on approximately 60 cm³ of fluid, at a speed of 1200 revolutions per minute (rpm), for 60 minutes, and with an applied load of 15 kg. Three M50 steel balls with roundness specification of $6.35 \times 10^{-4}$ mm were used. During each test, the torque was monitored on a real time data acquisition basis for data analysis to yield the coefficient of friction. After completion of each run, optical microscope pictures of the wear scars on the three stationary balls were taken and the scar diameters measured. The wear scar diameters reported herein are averages of the scar diameters on the three stationary balls.

The following table exemplifies utility of the compounds of this invention as high temperature lubricants. The smaller scar diameters and coefficients of friction exhibited by the compounds are evidence of better lubricity relative to 5P4E.

| Material | Wear scar diameter (mm) | Coefficient of friction |
|---|---|---|
| Polyphenyl Ether (5P4E) | 1.047 | 0.154 |
| 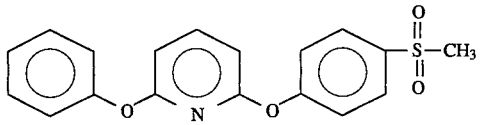 pyridine:2-(4-methylsulfonyl)-phenoxy)-6-phenoxy | 0.792 | 0.080 |
| 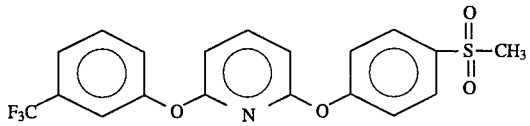 pyridine:2-(4-methylsulfonyl)-phenoxy)-6-(3-trifluoromethyl-phenoxy | 0.422 | 0.091 |
| 70 wt. % 5P4E + 30 wt. % 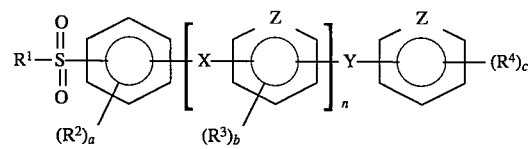 | 0.470 | |

What is claimed is:

1. An alkyl aryl sulfone of the formula:

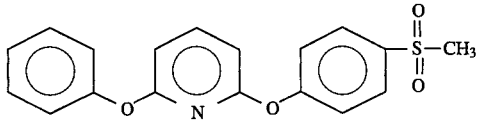

wherein Z is independently in each occurrence carbon or nitrogen;

R¹ is selected from the group $CH_3$ and $C_mF_{2m+1}$;

R² is independently in each occurrence a substituent selected from the group F, $C_mF_{2m+1}$, $OC_mF_{2m+1}$, phenyl, and phenoxy; a is 0 or an integer less than or equal to 4 inclusive;

R³ is independently in each occurrence a substituent selected from the group F, $C_mF_{2m+1}$, $OC_mF_{2m+1}$, phenyl, and phenoxy; b is 0 or an integer less than or equal to 4 inclusive when Z is carbon, and 0 or an integer less than or equal to 3 inclusive when Z is nitrogen;

R⁴ is independently in each occurrence a substituent selected from the group F, $C_mF_{2m+1}$, $OC_mF_{2m+1}$, and $$\overset{O}{\underset{O}{\overset{\|}{S}}}-R^1;$$

c is 0 or an integer less than or equal to 5 inclusive;
n is 0 or an integer less than or equal to 5 inclusive;
m is an integer from 1 to 10 inclusive; and X and Y are independently in each occurrence selected from the group: bond, O, $C(CH_3)_2$, $C(CF_3)_2$,

wherein R⁵ is independently in each occurrence an alkyl having from 1 to 12 carbon atoms inclusive, or an aryl having from 1 to 12 carbon atoms inclusive.

2. The alkyl aryl sulfone of claim 1 wherein Z is carbon in each occurrence.

3. The alkyl aryl sulfone of claim 2 wherein the alkyl aryl sulfone is 4-[4-(methylsulfonyl)phenoxy]phenyl phenyl sulfone, 4-[4-(trifluoromethylsulfonyl)phenoxy]phenyl phenyl sulfone, 4,4'-bis[4-(methylsulfonyl)phenoxy]phenyl sulfone, 4,4'-bis[ 4-(trifluoromethylsulfonyl)phenoxy]phenyl sulfone, 4,4'-bis[4-(methylsulfonyl)phenoxy]phenyl phenyl phosphine oxide, 4,4'-bis[4-(trifluoromethylsulfonyl)phenoxy]phenyl phenyl phosphine oxide, 4,4'-bis[4-(methylsulfonyl)phenoxy]phenyl methyl phosphine oxide, 4,4'-bis[4-(trifluoromethylsulfonyl) phenoxy]phenyl methyl phosphine oxide, 4-[4-(methylsulfonyl)phenoxy]biphenyl, 4-[4-(trifluoromethylsulfonyl)phenoxy] biphenyl, 4,4'-bis[4-(methylsulfonyl)phenoxy]biphenyl, 4,4'-bis[4-(trifluoromethylsulfonyl)phenoxy] biphenyl, 2[-4-(4-methylsulfonylphenoxy)phenyl] -2-phenylpropane, 2-[4-(4-methylsulfonylphenoxy)phenyl]- 2-phenyl-1,1,1,3,3,3-hexafluoropropane, 2,2-bis[4-(4-methylsulfonylphenoxy)phenyl]propane, 2,2-bis[4-(4-methylsulfonylphenoxy)phenyl-1,1,1,3,3,3-hexafluoropropane, 2-[4-(4-trifluoromethylsulfonylphenoxy)phenyl]-2-phenylpropane, -[4-(4-trifluoromethylsulfonylphenoxy)phenyl]-2-phenyl-1,1,1,3,3,3-hexafluoropropane, 2,2-bis[4-(4-trifluoromethylsulfonylphenoxy)phenyl]propane, or 2,2bis [4-(4-trifluoromethylsulfonylphenoxy)phenyl]-1,1,1,3,3,3-hexafluoropropane.

4. The alkyl aryl sulfone of claim 1 wherein at least one Z is nitrogen.

5. The alkyl aryl sulfone of claim 1 wherein $R^1$ is $CH_3$.

6. The alkyl aryl sulfone of claim 5 comprising:

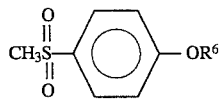

wherein $R^6$ is selected from the group Ph, $CF_3$Ph, FPh, 1,3-Ph, 1,4 Ph, PhOPh, FPhOPh, $CF_3$PhOPh, $CF_3$OPhOPh, Py, 2,4-Py, 6-($CF_3$PhO-2-Py), 6-(FPhO-2-Py);

Ph is phenyl; and

Py is pyridyl.

7. The alkyl aryl sulfone of claim 6 wherein the alkyl aryl sulfone is 1,3-bis(4-(methylsulfonyl)phenoxy)benzene, 2,6-bis-di[4-(methylsulfonyl)phenoxy]pyridine, 2-(4-methylsulfonylphenoxy)-6-(3-trifluoromethylphenoxy)pyridine, 2-phenoxy-6-(4-methylsulfonylphenoxy)pyridine, 4-(4-methylsulfonylphenoxy)benzophenone, 1-(4-methylsulfonyl)phenoxy)-4-phenoxy benzene, 1-(4-methylsulfonylphenoxy)-3-(3-(trifluoromethyl)phenoxy)benzene, or 1-(4-methylsulfonylphenoxy)-3-(3-(trifluoromethoxy)phenoxy)benzene.

8. The alkyl aryl sulfone of claim 1 wherein $R^1$ is $C_mF_{2m+1}$.

9. The alkyl aryl sulfone of claim 8 comprising:

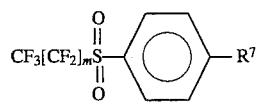

wherein $R^7$ is selected from the group PhO, PhOPhO, PhOPhOPhO, $CF_3$PhO, $CF_3$PhOPhO, $CF_3$PhOPyO, PhOPyO, FPhO, FPhOPhO, and $CF_3[CF_2]_mSO_2$PhO;

Ph is phenyl;

Py is pyridyl; and m is an integer from 1 to 10 inclusive.

10. The alkyl aryl sulfone of claim 9 wherein the alkyl aryl sulfone is 1-(3-phenoxyphenoxy)-4-(trifluoromethylsulfonyl)benzene, 1-(3-trifluoromethylphenoxy)-3-(4-(trifluoromethylsulfonyl)phenoxy)benzene, bis(3-(4-trifluoromethylsulfonylphenoxy)phenyl) ether, 1,3-bis( 4-(trifluoromethylsulfonyl)phenoxy)benzene, 2-phenoxy-6-( 4-( trifluoromethylsulfonyl)phenoxy)pyridine, benzene( 4-( 1,1,1,2,2-pentafluoroethylsulfonyl)phenoxy)-2-(3-trifluoromethylphenoxy), bis(4-(pentafluoroethylsulfonylphenoxyphenyl) ether, 1-(3-trifluoromethoxyphenoxy)-3-( 4-trifluoromethylsulfonyl)phenoxy)benzene, or (3-(4-pentafluoroethyl-sulfonylphenoxy)phenyl)(3-phenoxyphenyl) ether.

11. The alkyl aryl sulfone of claim 1 wherein $C_mF_{2m+1}$ and $OC_mF_{2m+1}$ are straight chain or branched chain moieties.

12. A lubricating mixture comprising a lubricant fluid and an alkyl aryl sulfone as described in claim 1 wherein the alkyl aryl sulfone is present in an amount sufficient to increase the lubricity of the lubricating mixture.

13. The lubricating mixture of claim 12 wherein the alkyl aryl sulfone is present in an amount, based on the weight of the lubricating fluid, of at least about 0.1 percent.

14. The lubricating mixture of claim 12 wherein the lubricant fluid is a compound selected from the group: phosphazenes, polyaryl ethers, polyol esters, and poly alpha olefins.

15. The lubricating mixture of claim 12 wherein the lubricant fluid comprises a polyphenyl ether compound.

16. A process for lubricating a metal-containing surface which comprises applying an alkyl aryl sulfone, as described in claim 1, to the metal surface.

17. A magnetic recording medium comprising a substrate having a magnetic recording lamina deposited thereon, wherein the lamina comprises magnetic particles and at least one alkyl aryl sulfone as described in claim 1, and the alkyl aryl sulfone is present in an amount of at least 0.001 weight percent based on the total weight of the lamina.

18. The magnetic recording medium of claim 17 wherein the magnetic recording lamina is particulate.

19. The magnetic recording medium of claim 17 wherein the magnetic recording lamina is a thin film.

20. The magnetic recording medium of claim 17 wherein the magnetic recording lamina is a metal evaporated tape.

21. A process for lubricating a magnetic recording medium comprising applying at least one lubricating mixture, as described in claim 12, to a surface of the magnetic recording medium to provide a lubricant film having an average thickness of 1 to 2000 Angstroms ($10^{-10}$ to $10^{-7}$ meters) on the surface.

22. A process for lubricating a magnetic recording medium comprising incorporating at least one alkyl aryl sulfone into a particulate magnetic recording lamina during preparation of the magnetic recording media so that the particulate magnetic recording lamina contains 0.001 to 10 weight percent of alkyl aryl sulfone as described in claim 1.

* * * * *